(12) United States Patent
Arnaud et al.

(10) Patent No.: US 6,203,780 B1
(45) Date of Patent: Mar. 20, 2001

(54) COSMETIC OR DERMATOLOGICAL COMPOSITION CONTAINING AT LEAST ONE FLUOROSILICONE WITH AN ALKYL CHAIN

(75) Inventors: Pascal Arnaud, L'Hay les Roses; Isabelle Bara, Paris, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/104,384

(22) Filed: Jun. 25, 1998

(30) Foreign Application Priority Data

Jun. 26, 1997 (FR) .................................................. 97 08027

(51) Int. Cl.$^7$ .......................... A61K 7/043; A61K 7/027; A61K 7/00; A61K 31/695
(52) U.S. Cl. ........................... 424/61; 424/64; 424/70.12; 424/401; 514/63
(58) Field of Search ................................ 424/401, 64, 61, 424/70.12; 514/63

(56) References Cited

U.S. PATENT DOCUMENTS

| | | | |
|---|---|---|---|
| 5,118,496 | * | 6/1992 | Herstein .................................. 424/63 |
| 5,401,309 | * | 3/1995 | Chopin et al. ....................... 106/461 |
| 5,473,038 | | 12/1995 | O'Lenick, Jr. . |
| 5,567,428 | * | 10/1996 | Hughes ................................. 424/401 |
| 5,800,816 | * | 9/1998 | Brieva et al. .......................... 424/63 |
| 5,851,539 | * | 12/1998 | Mellul et al. ....................... 424/401 |

FOREIGN PATENT DOCUMENTS

| | | |
|---|---|---|
| 0 511 092 | 10/1992 | (EP) . |
| 0 640 644 | 3/1995 | (EP) . |
| 0 657 486 | 6/1995 | (EP) . |

* cited by examiner

Primary Examiner—Diana Dudash
Assistant Examiner—Alysia Berman
(74) Attorney, Agent, or Firm—Nixon & Vanderhye P.C.

(57) ABSTRACT

The present invention provides cosmetic and dermatological compositions, and methods, containing at least one fluoro-alklsilicone of formula (I) and/or (II).

16 Claims, No Drawings

COSMETIC OR DERMATOLOGICAL COMPOSITION CONTAINING AT LEAST ONE FLUOROSILICONE WITH AN ALKYL CHAIN

The present invention relates to a cosmetic or dermatological composition containing a fluorosilicone with an alkyl chain, as an ingredient capable of enhancing various essential properties thereof.

It has already been proposed to use fluoro compounds in cosmetic compositions for their film-forming properties, as well as for their properties of softness and of remanence with respect to water.

Thus, EP-390,206 and EP-494,412 have described the use of hydrocarbon-based perfluoropolymers in various types of cosmetic compositions. However, these hydrocarbon-based perfluoropolymers have a relatively restricted spectrum of chemical compatibility, in particular with fatty substances, which thus limits the choice of starting materials with which they can be combined, and the nature of the compositions containing them. Furthermore, they can only be present in a relatively low proportion in cosmetic compositions.

JP-7-103,582 and JP-2-295,913 have also proposed the use of fluorosilicones in cosmetic compositions, but these also have relatively restricted compatibility spectra, which likewise limits the choice of ingredients with which they can be combined, as well as the proportions in which they can be present in the compositions.

It has now been discovered that a particular family of fluorosilicones, namely fluorosilicones containing a $C_6$–$C_{22}$ alkyl chain (referred to hereinbelow as fluoroalkylsilicones), has properties that are advantageous in terms of cosmetic or dermatological use. In particular, fluoroalkylsilicones can be good film-forming agents, leading, after application, to the formation of a film which is, at the same time, homogeneous, continuous, remanent with respect to water and which also has an excellent compromise between its durability and its ease of removal. The fluoroalkylsilicones of the compositions according to the invention also constitute lubricants, as well as very satisfactory binders.

Furthermore, these fluoroalkylsilicones have a much wider compatibility spectrum than fluoro compounds such as the fluorosilicones and perfluoroethers described in the prior art, thereby making it possible to prepare compositions using substances which could not be used hitherto.

They can also be introduced into compositions in a larger proportion without, however, affecting their homogeneity or their other properties, but, quite to the contrary, enhancing them.

The subject of the present invention is thus a cosmetic or dermatological composition containing, as ingredient, at least one fluoroalkylsilicone corresponding to one of the formulae (I) and/or (II) below:

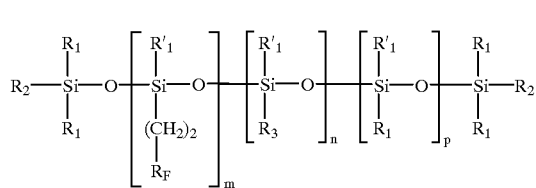
(I)

in which:
$R_1$ and $R'_1$ independently represent a linear or branched alkyl radical having from 1 to 6 carbon atoms or a phenyl radical, $R_2$ represents $R_1$, —OH or —$(CH_2)_f$—RF, f being an integer ranging from 0 to 10, $R_3$ represents a linear or branched alkyl radical having from 6 to 22 carbon atoms, $R_F$ represents a radical of formula —$(CF_2)_q$—$CF_3$, q being an integer ranging from 0 to 10, m and n represent an integer ranging from 1 to 50, and p represents an integer ranging from 0 to 2000,

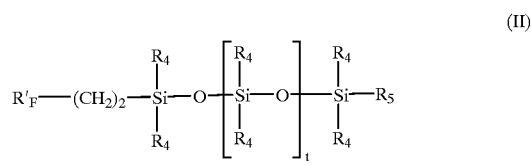
(II)

in which:
$R_4$ represents a linear or branched alkyl radical having from 1 to 6 carbon atoms, or a phenyl radical, $R_5$ represents a linear or branched alkyl radical having from 6 to 22 carbon atoms, $R'_F$ represents a radical of formula —$(CF_2)_s$—$CF_3$, s being an integer ranging from 0 to 15, and t represents an integer ranging from 1 to 2000.

According to a particular embodiment of the cosmetic compositions according to the invention, the fluoroalkylsilicone corresponds to formula (I) in which:

$R_1$, $R'_1$ and $R_2$ represent a methyl radical, $R_3$ represents a linear alkyl radical having from 6 to 22 carbon atoms, m and n are integers ranging from 1 to 20, and q is an integer ranging from 1 to 13.

According to another embodiment of the compositions according to the invention, the fluoroalkylsilicone corresponds to formula (II) in which:

$R_4$ represents a methyl radical, $R_5$ represents a linear alkyl radical having from 6 to 22 carbon atoms, and s represents an integer ranging from 1 to 13.

The fluoroalkylsilicones as defined above are known compounds which have been described in particular in U.S. Pat. No. 5,473,038.

In the compositions according to the invention, the fluoroalkylsilicone as defined above is generally present in a proportion ranging from 0.1 to 99% by weight, but preferably from 1 to 80% by weight, relative to the total weight of the composition.

According to a first particular embodiment of the invention, the compositions are anhydrous and comprise a fatty phase in a proportion ranging from 0.1 to 99.9% by weight relative to the total weight of the composition, the said fatty phase containing:

(i) from 0.1 to 99.9% by weight, relative to the total weight of the said composition, of a fluoroalkylsilicone of formula (I) and/or (II), and (ii) from 0 to 99.8% by weight, relative to the total weight of the said composition, of at least one liquid, solid or semisolid fatty substance.

This or these fatty substance(s) can be selected from oils, waxes, gums and/or so-called pasty fatty substances.

A—The oils of the fatty phase can be of mineral, animal, plant or synthetic origin, it being possible for these oils to be volatile or non-volatile at room temperature.

As oils of mineral origin, mention may be made in particular of liquid paraffin and liquid petroleum jelly.

As oils of animal origin, mention may be made in particular of squalane or perhydrosqualene.

As oils of plant origin, mention may be made in particular of sweet almond oil, beauty-leaf oil, palm oil, avocado oil, jojoba oil, sesame oil, olive oil, castor oil and cereal germ oils such as, for example, wheatgerm oil.

As synthetic oils, mention may be made in particular of:

(1) esters of formula:

$$R_6\text{—COOR}_7$$

in which:

$R_6$ represents the residue of a higher fatty acid having from 7 to 20 carbon atoms and $R_7$ represents a hydrocarbon-based radical having from 3 to 30 carbon atoms.

Among these esters, mention may be made in particular of: purcellin oil, butyl myristate, isopropyl myristate, cetyl myristate, isopropyl palmitate, butyl stearate, hexadecyl stearate, isopropyl stearate, octyl stearate, isocetyl stearate, decyl oleate, hexyl laurate, isononyl isononanoate, esters derived from lanolic acid, such as isopropyl lanolate and isocetyl lanolate.

As other synthetic oils, mention may also be made of isododecane, isohexadecane, polyisobutenes and hydrogenated polyisobutene, as well as acetyl glycerides, octanoates and decanoates of polyalcohols such as those of glycol and of glycerol, ricinoleates of alcohols and of polyalcohols such as that of cetyl alcohol, propylene glycol dicaprylate and diisopropyl adipate;

(2) fatty alcohols such as oleyl alcohol, linoleyl alcohol, linolenyl alcohol, isostearyl alcohol and octyldodecanol;

(3) silicone oils such as linear, optionally functionalized polydiorganosiloxanes, cyclic polydiorganosiloxanes and in particular cyclotetra- and penta-dimethicones and organopolysiloxanes such as alkyl-, alkoxy- or phenyl-dimethicones and in particular phenyltrimethicone;

(4) fluoro oils such as perfluoroalkanes and perfluoropolyethers and partially fluorinated hydrocarbon-based oils.

B—Waxes of the fatty phase can be of mineral, fossil, animal, plant or synthetic origin or alternatively can be hydrogenated oils or fatty esters that are solid at 25° C.

Among the mineral waxes, mention may be made in particular of microcrystalline waxes, paraffin, petroleum jelly and ceresine.

Among the fossil waxes, mention may be made of ozokerite and montan wax.

Among the waxes of animal origin, mention may be made of beeswax, spermaceti, lanolin wax and lanolin derivatives such as lanolin alcohols, hydrogenated lanolin, hydroxylated lanolin, acetylated lanolin, lanolin fatty acids and acetylated lanolin alcohol.

Among the waxes of plant origin, mention may be made in particular of candelilla wax, carnauba wax, Japan wax and cocoa butter.

Among the synthetic waxes, mention may be made in particular of ethylene homopolymers and copolymers of ethylene with a monomer corresponding to the formula:

$$CH_2\text{=}CH\text{—}R_8 \qquad (III)$$

in which:

$R_8$ represents an alkyl radical having from 1 to 30 carbon atoms or an aryl or aralkyl radical.

The alkyl radical having from 1 to 30 carbon atoms is preferably a methyl, ethyl, propyl, isopropyl, butyl, decyl, dodecyl or octadecyl radical.

Waxes obtained by Fisher-Tropsch synthesis and silicone waxes can also be used.

Among the hydrogenated oils that are solid at 25° C., mention may be made in particular of hydrogenated castor oil, hydrogenated palm oil, hydrogenated tallow and hydrogenated coconut oil.

Among the fatty esters that are solid at 25° C., mention may be made in particular of propylene glycol monomyristate and myristyl myristate.

As waxes which can be used in the compositions according to the invention, mention may also be made of cetyl alcohol, stearyl alcohol, mono-, di- and triglycerides that are solid at 25° C., stearic monoethanolamide, colophony and its derivatives such as glycol abietates and glyceryl abietates, sucroglycerides and calcium, magnesium, zinc and aluminium oleates, myristates, lanolates, stearates and dihydroxystearates.

C—The fatty substances of pasty type can be of mineral, animal, plant or synthetic origin.

Among the pasty fatty substances, mention may be made in particular of synthetic esters such as arachidyl propionate, polyvinyl laurate, polyethylene waxes and organopolysiloxanes such as alkyldimethicones, alkoxydimethicones or dimethicone esters.

Of the various fatty substances listed above, the following are preferably used according to the invention:

(1) among the oils: isododecane, hydrogenated polyisobutene, squalane, isononyl isononanoate, cyclomethicones such as cyclotetra- and -penta-dimethicones and phenyltrimethicone;

(2) among the waxes:

(i) ethylene homopolymers having a weight-average molecular mass of between 200 and 1000 and in particular those sold under the names "Polywax 500" and "Polywax 655" by the company Bareco, (ii) copolymers of ethylene with at least one monomer of formula (III) in which the radical $R_8$ represents a methyl, ethyl, isopropyl, butyl, dodecyl or octadecyl radical, these copolymers having a weight-average molecular mass of between 200 and 1000. Among these, mention may be made of ethylene/propylene copolymers such as those sold under the names "Petrolite CP-7" and "Petrolite CP-12" by the company Bareco and ethylene/hexene copolymers such as those sold under the names "Petrolite CH-7" and "Petrolite CH-12" by the company Bareco, (iii) microcrystalline waxes and ozokerite, (iv) beeswax;

(3) as pasty fatty substances, arachidyl propionate.

The anhydrous compositions according to the invention can, needless to say, also contain one or more cosmetically or dermatologically conventional additives or adjuvants.

These anhydrous compositions can be in various forms such as, in particular, in the form of an oily gel, in the form of solid products such as compacted or cast powders, or alternatively in the form of sticks such as, for example, lipsticks.

When the compositions according to the invention are in the form of an oily gel, they generally contain, besides the constituents defined above, an oily gelling agent.

Among the oily gelling agents, mention may be made in particular of metal esters such as polyoxyaluminium stearate and aluminium or magnesium hydroxystearate, fatty acid esters of glycol, triglycerides, mixtures of fatty alcohols, cholesterol derivatives and in particular hydroxycholesterol, and inorganic clays which swell in the presence of oil, and in particular those belonging to the montmorillonite group.

The oily gelling agents can be present in a very variable proportion depending on the desired texture of the compositions. However, in most cases, they are present in a proportion ranging from 0.1 to 30% by weight relative to the total weight of the composition.

These anhydrous compositions according to the invention can be used in particular as care products, cleansing products, make-up-removing products or make-up products.

When they are in the form of make-up products, they can be, in particular, foundations, mascaras, eyeliners, lipsticks, eyeshadows or blushers. These compositions are generally coloured and, in this case, contain, as cosmetic adjuvants, dyes and/or pigments that are well known in the field of make-up products.

According to a second embodiment of the invention, the compositions are dispersions in the form of a stable water-in-oil (W/O) or oil-in-water (O/W) emulsion consisting essentially (i) of a fatty phase in a proportion ranging from 0.1 to 50% by weight relative to the total weight of the composition, the said fatty phase containing a fluoroalkylsilicone of formula (I) and/or (II) as defined above in a proportion ranging from 0.1 to 50% by weight relative to the total weight of the composition, (ii) an aqueous phase in a proportion ranging from 50 to 98.9% by weight relative to the total weight of the composition, and (iii) at least one emulsifier in a proportion ranging from 1 to 10% by weight relative to the total weight of the composition in emulsion form.

It has been observed that, in contrast with the fluoro oils used previously, the fluoroalkylsilicones of formula (I) and/or (II) make it possible to obtain emulsions that are very stable over time, this being irrespective of the storage conditions.

As emulsifier or surfactant which can be used in the compositions according to the invention of the W/O or O/W emulsion type, mention may be made in particular of silicone surfactants, and in particular those belonging to the family of alkyl- or alkoxy-dimethicone copolyols. Among the alkyl- or alkoxy-dimethicone copolyols mention may be made in particular of the compounds corresponding to the following general formula:

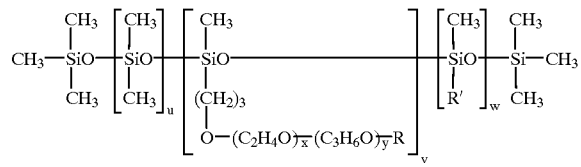

(IV)

in which:
R is a hydrogen atom, a $C_1$–$C_{16}$ alkyl, an alkoxy or an acyl,
R' is a $C_8$–$C_{22}$ alkyl or alkoxy radical,
u=0 to 200,
v=1 to 40,
w=1 to 100,
the molecular weight of the radical —O—$(C_2H_4O)_x$—$(C_3H_6O)_y$—R being from 250 to 2000, x and y being chosen such that the weight ratio of the oxyethylene/oxypropylene groups is between 100:0 and 20:80.

Among the commercial products which can contain all or part of the alkyldimethicone copolyols which can be used according to the invention, mention may be made in particular of those sold under the names "Abil WE09", "Abil EM90" or "Abil WS08" by the company Goldschmidt, "Q2 5200" or "Q2 3225C" by the company Dow Corning and "218 1138" by the company General Electric.

These emulsions are preferably in the form of creams and can be used as care products, cleansing products or make-up products.

They can also constitute products for protecting the skin against various types of attack by virtue of the excellent quality of the film formed by the fluoroalkylsilicone of formula (I) and/or (II) after application. The compositions according to the invention can also constitute excellent antisun products when UVA and/or UVB screening agents and/or nanometer-sized pigments are introduced therein.

When these compositions are make-up products, they can be, in particular, foundations in which case they contain a certain proportion of pigments and/or dyes.

Whether anhydrous or not, the compositions according to the invention have excellent cosmetic properties such as, in particular, better ease of application and great softness, and lead to the production of a uniform make-up effect.

These make-up compositions moreover have excellent resistance to transfer onto a support other than the one on which they have been applied. The term transfer is understood to refer to the displacement of a fraction of the composition by contact with another support, whether or not it is of the same nature. Needless to say, this property is particularly advantageous when the compositions are highly coloured. For example, when the make-up compositions are eyeshadows, eyeliners or mascaras, this property avoids transfer of the compositions onto the hands by rubbing or by contact of the hands with the eyes. For the compositions in the form of lipsticks, this property makes it possible to limit the transfer of the lipstick onto the hands or alternatively onto the cheeks of another person. Moreover, this property also makes it possible to avoid marking napkins and to avoid leaving imprints on glasses, cups and the like.

When the compositions according to the invention are foundations, this property makes it possible in particular to prevent the transfer of the foundation onto shirt collars and thus to avoid marking them.

According to a third embodiment of the compositions according to the invention, they are in the form of products for the nails, such as nail varnishes, or nailcare products comprising a fluoroalkylsilicone of formula (I) and/or (II) as defined above, in a proportion ranging from 0.1 to 99.9% by weight relative to the total weight of the composition.

Preferably, according to this embodiment, the compositions are in the form of a nail varnish and contain:
(i) a fluoroalkylsilicone of formula (I) and/or
  (II) in a proportion ranging from 2 to 40% by weight relative to the total weight of the varnish,
(ii) a solvent system for varnishes, and
(iii) a film-forming substance.

According to this embodiment, the solvent system for the varnish is generally present in a proportion ranging from 55 to 90% by weight relative to the total weight of the varnish.

Although the solvent system can be of the aqueous type, it preferably consists of a mixture of various volatile organic solvents, this being in order to obtain relatively short drying times.

Among these solvents, mention may be made of acetone, ethyl acetate, butyl acetate, 2-methoxyethyl acetate, methyl ethyl ketone, methyl isobutyl ketone, methyl acetate, amyl acetate and isopropyl acetate.

The solvent system can also comprise a diluent which is preferably a saturated, linear or branched hydrocarbon, such as hexane or octane, or alternatively an aromatic hydrocarbon such as toluene or xylene, in a proportion generally ranging from 10 to 35% by weight relative to the total weight of the varnish. The solvent system can also include other volatile solvents such as ethanol, n-butanol, n-propanol and isopropanol, or mixtures thereof.

Besides the fluoroalkylsilicone of formula (I) and/or (II), the composition according to the invention can also comprise a film-forming substance. This film-forming substance is generally present in a proportion ranging from 5 to 35% by weight relative to the total weight of the varnish. Among these film-forming substances, mention may be made of nitrocelluloses of the "RS" or "SS" type and in particular nitrocellulose type ¼ second RS, nitrocellulose type ½ second RS, nitrocellulose type ½ second SS and nitrocellulose type ¾ second RS. As film-forming substances, polyvinyl derivatives such as polyvinyl butyrate can also be used according to the invention.

As other film-forming substances, cellulose derivatives other than nitrocellulose, acrylic polymers or copolymers, resins of the acrylic, styrene, vinyl and styrene-acrylate type, vinyl copolymers, polyester polymers, resins of the arylsulphonamide type and alkyd resins can be used according to the invention.

Varnishes according to the invention can also contain a plasticizer which is generally present in a proportion ranging from 5 to 20% by weight relative to the total weight of the varnish. The plasticizers make it possible to fix the flexibility of the film without weakening its resistance or its physical strength. Among the plasticizers, mention may be made of: tricresyl phosphate, benzyl benzoate, tributyl phosphate, butyl acetylricinoleate, triethyl citrate, tributyl acetyl citrate, dibutyl phthalate and camphor.

The products for the nails according to the invention can be either colourless or coloured. When they are coloured, they then contain pigments and/or dyes that are well known in the field of nail varnishes.

According to a fourth particular embodiment of the compositions according to the invention, they are hair compositions containing, in a cosmetic vehicle chosen from alcoholic and aqueous-alcoholic solutions, at least one fluoroalkylsilicone of formula (I) and/or (II) as defined above, in a proportion ranging from 60 to 99.5% by weight relative to the total weight of the composition.

The alcohol is preferably ethanol or isopropanol, which is generally present in the aqueous-alcoholic solutions in a proportion ranging from 60 to 99.5% by weight relative to the total weight.

These hair compositions in the form of lotions to be sprayed or in aerosol form are readily applied and form a continuous and uniform film which allows very satisfactory coating of the hair, but which is nevertheless easily removed by shampooing. The hair compositions according to the invention can also contain various additives and ingredients used in the field of hair treatment such as, in particular, UV screening agents, and can thus constitute compositions intended in particular for protecting dyed hair against harmful effects of the sun.

Although reference has been made above more particularly to lotions, the hair compositions according to the invention can also be in the form of fluid emulsions which allow good impregnation of the hair.

The compositions according to the invention, as have just been described above, can also contain one or more conventional cosmetic adjuvants such as vitamins, hormones, antioxidants, preserving agents, fillers, fragrances, thickeners, moisturizers, wetting agents, anionic, nonionic or amphoteric polymers, or cosmetic or dermatological active agents.

Among these adjuvants, the charges are generally present in the care or make-up products or in the dermatological products in a maximum proportion of about 99.9% by weight relative to the total weight of the composition.

These fillers, in the form of very fine powders, can be of natural or synthetic origin. Among these fillers, mention may be made in particular of:

a) mineral powders such as talc, kaolin, mica, silica, silicates, alumina, zeolites, hydroxyapatite, sericite, titanium dioxide, titanium micas, barium sulphate, bismuth oxychloride, boron nitride and metal powders such as aluminium powder;

b) plant powders such as corn starch powder, wheat starch powder or rice starch powder;

c) organic powders such as nylon powder, polyamide powder, polyester powder, polytetrafluoroethylene powder or polyethylene powder.

These various powders can also be coated, for example with metal salts of fatty acids, amino acids, lecithin, collagen, silicone compounds or fluoro compounds, or any other common coating agent.

Besides fillers, dyes and pigments also not only form part of the anhydrous or dispersed make-up compositions but also form part of nail varnishes. The dyes and/or pigments are generally present in a maximum proportion of about 40% relative to the total weight of the composition.

In lipsticks, the proportion of at least one dye and/or pigment is generally about 0.1 to 15% by weight relative to the total weight of the lipstick.

Among the dyes for the make-up products and in particular for lipsticks, mention may be made of eosin derivatives such as D&C Red No. 21 and halogenated fluorescein derivatives such as D&C Red No. 27, D&C Red Orange No. 5 in combination with D&C Red No. 21 and D&C Orange No. 10.

Among the pigments which can be inorganic or organic or alternatively metal lakes, mention may be made of titanium dioxide, zinc oxide, D&C Red No. 36 and D&C Orange No. 17, the calcium lakes of D&C Red No. 7, 11, 31 and 34, the barium lake of D&C Red No. 12, the strontium lake D&C Red No. 13, the aluminium lakes of FD&C Yellow No. 5, FD&C Yellow No. 6, D&C Red No. 27, D&C Red No. 21, FD&C Blue No. 1, iron oxides, manganese violet, chromium oxide and ultramarine blue.

Among the nail varnish pigments most frequently used, mention may be made of D&C Red No. 8, 10, 30 and 36, the barium lakes of D&C Red No. 6, 9 and 12, the calcium lakes of D&C Red No. 7, 11, 31 and 34, the strontium lake of D&C Red No. 30 and D&C Orange No. 17 and D&C Blue No. 6.

The nail varnishes can also contain titanium dioxide in order to give the varnishes a certain level of opacity, as well as certain iridescent substances such as guanine and products which make it possible to avoid the sedimentation of the pigments, such as modified montmorillonite clays such as, for example, Bentone 27, Bentone 34 or Bentone 38.

The invention will now be illustrated with the aid of the various examples which follow, in which the amounts are expressed on a weight basis.

EXAMPLE 1

Transfer-resistant Lipstick

A lipstick is prepared by mixing together the following ingredients:

| Phase A | |
|---|---|
| Fluoroalkylsilicone (a) | 20 g |
| Arachidyl propionate | 9 g |
| Ethylene homopolymer sold under the name "Polywax 500" by the company Bareco | 16 g |
| Phase B | |
| Cyclotetradimethicone sold under the name "Dow Corning 244 Fluid" by the company Dow Corning | 46 g |
| Phase C | |
| Pigments | 9 g |

(a) Fluoroalkylsilicone of formula (I) in which $R_1$, $R'_1$ and $R_2$ represent a methyl radical, $R_3$ represents a linear alkyl radical having 16 carbon atoms, $R_F$ represents —$(CF_2)_q$—$CF_3$, q is equal to 5, m, n and p are respectively equal to 10, 20 and 50.

This lipstick is prepared by heating the ingredients of Phase A to a temperature of about 95° C. After complete melting, the pigments (Phase C) are added, followed, at 60° C., by addition of Phase B. The mixture is then homogenized using a Moritz-type turbomixer at a speed of 3000 rpm. The homogeneous mixture obtained can then be cast at 85° C. into cells for lipsticks.

After cooling, the lipsticks are removed from the cells.

The lipsticks obtained apply very easily to the lips, to which they impart very great softness. After application, the lipsticks also have excellent staying power, i.e. excellent resistance to wear. Furthermore, they have good transfer resistance.

EXAMPLE 2

Transfer-resistant Lipstick

This lipstick is obtained according to the same procedure as that described in Example 1, using the following phases:

| Phase A | |
|---|---|
| Fluoroalkylsilicone (b) | 20 g |
| Arachidyl propionate | 9 g |
| Ethylene homopolymer sold under the name "Polywax 500" by the company Bareco | 16 g |
| Phase B | |
| Cyclotetradimethicone sold under the name "Dow Corning 244 fluid" by the company Dow Corning | 46 g |
| Phase C | |
| Pigments | 9 g |

(b) Fluoroalkylsilicone of formula (II) in which $R_4$ represents a methyl radical, $R_5$ represents a linear alkyl radical having 16 carbon atoms, $R'_F$ represents —$(CF_2)_8$—$CF_3$ and t is equal to 1.

This lipstick, which differs from the previous one by the nature of the fluoroalkylsilicone, has excellent staying power and comfort properties.

EXAMPLE 3

Transfer-resistant Lipstick

According to the conventional method for the preparation of lipsticks, the following various ingredients were mixed together:

| Fluoroalkylsilicone (idem Example 1) | 8 g |
|---|---|
| Hydrogenated polyisobutene | 28 g |
| Polybutene | 10 g |
| Diisostearyl malate | 5 g |
| Octyldodecanol | 5 g |
| Lanolin oxypropylenated with 5 mol of propylene oxide | 5 g |
| Modified hectorite (Bentone) | 0.8 g |
| Ethylene homopolymer sold under the name "Polywax 500" by the company Bareco | 11 g |
| Octacosanyl stearate | 4 g |
| Hydrogenated coconut oil | 5 g |
| Polydimethylsiloxane (5 cst) | 9.54 g |
| Pigments | 8.6 |

The lipstick obtained has great softness when applied and leads to the production of a light, comfortable and non-greasy film on the lips.

EXAMPLE 4

Foundation

A foundation in the form of a water-in-oil (W/O) emulsion is prepared with the aid of the following ingredients:

| Fatty phase A | |
|---|---|
| Poly(4-glyceryl isostearate) and cetyldimethicone copolyol and hexyl laurate sold under the name "Abil WE09" by the company Goldschmidt | 5 g |
| Fluoroalkylsilicone (idem Example 1) | 15 g |
| Pigments (iron oxide and titanium dioxide) coated with polydimethylsiloxanes | 7 g |
| Aqueous phase B | |
| Preserving agent q.s. | |
| Water q.s. | 100 g |

This W/O emulsion is obtained by dispersing the pigments in the fatty phase at room temperature. The aqueous phase B is then incorporated therein with stirring, using a Moritz-type turbomixer at a speed of 3000 rpm.

EXAMPLE 5

A pearlescent nail varnish is prepared using the following ingredients:

| Nitrocellulose | 12 g |
|---|---|
| Alkyd resin | 5 g |
| Tributyl acetyl citrate | 3 g |
| Fluoroalkylsilicone (idem Example 1) | 3 g |
| Isopropyl alcohol | 8 g |
| Hectorite | 1 g |
| Pearlescent pigments | 0.5 g |
| Ethyl acetate/butyl acetate q.s. | 100 g |

This varnish is obtained with vigorous stirring and under pressure by dispersing the hectorite in some of the nitrocellulose and the mixture of acetates, followed by addition of the rest of the ingredients.

What is claimed is:

1. A stable cosmetic or dermatological composition, containing as film forming agent at least one fluoroalkylsilicone selected from the group consisting of fluoroalkylsilicone of formula (I):

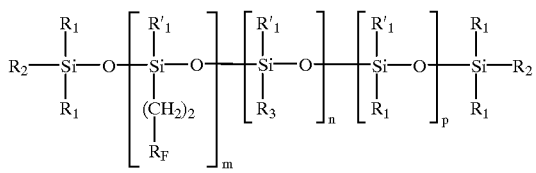

(I)

in which:

R$_1$ and R'$_1$ independently represent a linear or branched alkyl radical having from 1 to 6 carbon atoms or a phenyl radical, R$_2$ represents R$_1$, —OH or —(CH$_2$)$_f$—R$_F$, f being an integer ranging from 0 to 10, R$_3$ represents a linear or branched alkyl radical having from 6 to 22 carbon atoms, R$_F$ represents a radical of formula —(CF$_2$)$_q$—CF$_3$, q being an integer ranging from 0 to 15, m and n represent an integer ranging from 1 to 50, and p represents an integer ranging from 0 to 2000, and fluoroalkylsilicone of formula (II):

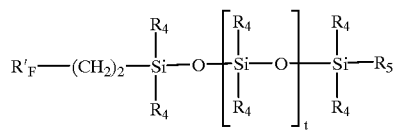

(II)

in which:

R$_4$ represents a linear or branched alkyl radical having from 1 to 6 carbon atoms, or a phenyl radical, R$_5$ represents a linear or branched alkyl radical having from 6 to 22 carbon atoms, R'$_F$ represents a radical of formula —(CF$_2$)$_s$—CF$_3$, s being an integer ranging from 0 to 15, and t represents an integer ranging from 1 to 2000, in a suitable cosmetic or dermatoloigcal carrier.

2. The composition according to claim 1, wherein the said fluoroalkylsilicone is corresponding to formula (I) wherein:

R$_1$, R'$_1$ and R$_2$ represent a methyl radical,

R$_3$ represents a linear alkyl radical having from 6 to 22 carbon atoms, m and n are integers ranging from 1 to 20, and q is an integer ranging from 1 to 13.

3. The composition according to claim 1, wherein the said fluoroalkylsilicone is corresponding to formula (II) wherein:

R$_4$ represents a methyl radical,

R$_5$ represents a linear alkyl radical having from 6 to 22 carbon atoms, and s represents an integer ranging from 1 to 13.

4. The composition according to claim 1 wherein said fluoroalkylsilicone is present in a proportion ranging from 0.1 to 99% by weight relative to the total weight of the composition.

5. The composition according to claim 1, wherein said composition is anhydrous and contains a fatty phase in a proportion ranging from 0.1 to 99.9% by weight relative to the total weight of the composition, the said fatty phase containing:

(i) from 0.1 to 99.9% by weight, relative to the total weight of the composition, of a fluoroalkylsilicone selected from the group consisting of formula (I) and (II), and (ii) the remaining up to 99.8% by weight, relative to the total weight of the composition, of at least one liquid, solid or semisolid fatty substance.

6. The composition according to claim 5, wherein the said fatty substance is seleced from the group consisting of isododecane, hydrogenated polyisobutene, squalane, isononyl isononanoate, cyclotetra- and -pentadimethicones, phenyltrimethicone, ethylene homopolymers, copolymers of ethylene with at least one monomer corresponding to formula (III) below:

$$CH_2=CH-R_8 \qquad (III)$$

Wherein:

R$_8$ represents an alkyl radical having from 1 to 30 carbon atoms, an aryl or aralkyl radical, the said homopolymers and copolymers having a weight-average molecular mass of between 200 and 1000, microcrystalline waxes, ozokerite, beeswax, candelilla wax and arachidyl propionate.

7. The composition according to claim 1, which is in the form of an oily gel, a compacted powder, a cast powder or a stick.

8. The composition according to claim 7, wherein the stick is a lipstick containing at least one substance selected from the group consisting of a dye and pigment in a proportion ranging from 0.5 to 15% by weight relative to the total weight of the composition in lipstick form.

9. The composition according to claim 1, which is in the form of a stable water-in-oil or oil-in-water dispersion, comprising (i) a fatty phase in a proportion ranging from 0.1 to 50% by weight relative to the total weight of the composition, the said fatty phase containing a fluoroalkyl-silicone selected from the group consisting of formula (I) and (II) in a proportion ranging from 0.1 to 50% by weight relative to the total weight of the composition, (ii) an aqueous phase in a proportion ranging from 50 to 98.9% by weight relative to the total weight of the composition, and (iii) at least one emulsifier in a proportion ranging from 1 to 10% by weight relative to the total weight of the composition.

10. The composition according to claim 9, wherein the said fatty phase contains at least one fatty substance.

11. The composition according to claim 9, wherein the said emulsifier is selected from the group consisting of alkyl- and alkoxy-dimethicone copolyols of the following general formula:

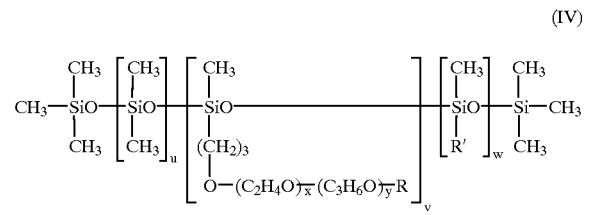

(IV)

wherein:

R is a hydrogen atom, a C$_1$–C$_{16}$ alkyl, an alkoxy or an acyl,

R' is a C$_8$–C$_{22}$ alkyl or alkoxy radical, u=0 to 200, v=1 to 40, w=1 to 100, the molecular weight of the radical $-O-(C_2H_4O)_x-(C_3H_6O)_y-R$ being from 250 to 2000, x and y being selected such that the weight ratio of the oxyethylene/oxypropylene groups is between 100:0 and 20:80.

12. The composition according to claim 1, which is in the form of a make-up or nailcare composition containing a fluoroalkylsilicone selected from the group consisting of formula (I) and (II) in a proportion ranging from 0.1 to 99.9% by weight relative to the total weight of the composition.

13. The composition according to claim 12, which is in the form of a nail varnish and contains:

(i) a fluoroalkylsilicone selected from the group consisting of formula (I) and (II) in a proportion ranging from 2 to 40% by weight relative to the total weight of the varnish, (ii) a solvent mixture for varnishes, and (iii) a film-forming substance.

14. The composition according to claim 13, wherein the solvent mixture is present in a proportion ranging from 55 to 90% by weight and the film-forming substance is present in a proportion ranging from 5 to 35% by weight relative to the total weight of the composition in nail varnish form.

15. The composition according to claim 1, which is in the form of a hair care composition comprising, in a cosmetic vehicle selected from the group consisting of alcoholic and aqueous-alcoholic solutions, at least one fluoroalkylsilicone selected from the group consisting of formula (I) and (II) in a proportion ranging from 0.5 to 40% by weight relative to the total weight of the composition.

16. The composition according to claim 1, which further contains at least one conventional cosmetic adjuvant selected from the group consisting of fillers, UVA and/or UVB sunscreens, vitamins, hormones, antioxidants, preserving agents, dyes, pigments, fragrances, thickeners, moisturizers, wetting agents, anionic polymers, nonionic polymers, amphoteric polymers, cosmetic active substances and dermatological active substances.

* * * * *